(12) United States Patent
Collins (10) Patent No.: US 7,708,009 B1
(45) Date of Patent: May 4, 2010

(54) REUSABLE PERSONAL HEATING SYSTEM

(76) Inventor: Kenneth Randall Collins, 4652 Raleigh LaGrange, Memphis, TN (US) 38128

( * ) Notice: Subject to any disclaimer, the term of this patent is extended or adjusted under 35 U.S.C. 154(b) by 79 days.

(21) Appl. No.: 12/027,690

(22) Filed: Feb. 7, 2008

Related U.S. Application Data (60) Provisional application No. 60/888,800, filed on Feb. 8, 2007.

(51) Int. Cl.
*A61F 7/00* (2006.01)
*F24J 1/00* (2006.01)

(52) U.S. Cl. .............. 126/204; 126/263.07; 126/263.03
(58) Field of Classification Search ............. 126/204, 126/263.03, 263.07; 62/4; 206/304.1, 466; 422/245.1; 200/341, 337, 344, 511
See application file for complete search history.

(56) References Cited

U.S. PATENT DOCUMENTS

| | | | | |
|---|---|---|---|---|
| 1,609,958 A * | 12/1926 | Perrault | ................. | 126/263.02 |
| 4,128,194 A * | 12/1978 | Hinz | ........................... | 224/194 |
| 4,532,110 A * | 7/1985 | Kapralis et al. | .......... | 422/245.1 |
| 4,572,158 A * | 2/1986 | Fiedler | .................. | 126/263.04 |
| 4,731,883 A * | 3/1988 | Foster | ............................. | 2/69 |
| 4,899,727 A * | 2/1990 | Kapralis et al. | ........ | 126/263.04 |
| 5,038,779 A * | 8/1991 | Barry et al. | .................. | 607/108 |
| 5,199,555 A * | 4/1993 | Hirano | ........................ | 200/341 |
| 5,205,278 A * | 4/1993 | Wang | ...................... | 126/263.03 |
| 5,484,366 A * | 1/1996 | Wilkinson | ................... | 482/105 |
| 5,564,124 A * | 10/1996 | Elsherif et al. | .................... | 2/69 |
| 5,605,144 A * | 2/1997 | Simmons et al. | ............. | 126/204 |
| 6,283,116 B1 * | 9/2001 | Yang | ...................... | 126/263.03 |
| 6,795,976 B1 * | 9/2004 | van der Sleesen | ................. | 2/69 |
| 6,823,678 B1 * | 11/2004 | Li | .................. | 62/3.5 |
| 7,273,989 B2 * | 9/2007 | Martin Hernandez | ..... | 200/52 R |
| 7,329,822 B1 * | 2/2008 | Orrico | ...................... | 200/332.1 |
| 7,442,894 B2 * | 10/2008 | Villain et al. | ................ | 200/344 |
| 2005/0006215 A1 * | 1/2005 | Sasaki et al. | ................ | 200/344 |
| 2006/0036304 A1 * | 2/2006 | Cordani et al. | .............. | 607/108 |
| 2007/0106356 A1 * | 5/2007 | Carstens | ...................... | 607/112 |
| 2007/0278078 A1 * | 12/2007 | Mishima | ...................... | 200/344 |

* cited by examiner

*Primary Examiner*—Kenneth B Rinehart
*Assistant Examiner*—Frances Kamps
(74) *Attorney, Agent, or Firm*—Wyatt, Tarrant & Combs, LLP; H. Roy Berkenstock; Sharon Osborn Hill (57) ABSTRACT

The present invention generally relates to a reusable personal heating system including a sealed container filled with a supercooled supersaturated solution and an activator located in a fixed position within the container which triggers an exothermic crystallization process when depressed. The removable and reusable personal heating system fits into a garment worn under other clothing and is easily activated through other clothing. The present invention provides a personal heating system that allows the wearer to participate in outdoor activities in cold conditions while permitting ease of mobility and range of motion.

14 Claims, 10 Drawing Sheets

REUSABLE PERSONAL HEATING SYSTEM

CROSS REFERENCE TO RELATED APPLICATIONS

This application claims priority of U.S. Provisional Patent Application Ser. No. 60/888,800, filed on Feb. 8, 2007, which is hereby incorporated by reference.

STATEMENT REGARDING FEDERALLY SPONSORED RESEARCH OR DEVELOPMENT

Not applicable

REFERENCE TO A MICROFICHE APPENDIX

Not applicable

BACKGROUND OF THE INVENTION

The present invention generally relates to a reusable personal heating system filled with a supercooled supersaturated solution and including a trigger device and to a garment worn under other clothing containing a removable and reusable personal heating system easily accessible through other clothing.

It is beneficial for people participating in outdoor activities such as diving, motorcycle riding, hunting, fishing, water skiing, snow skiing, yard work, etc. to wear light-weight clothing which allows for ease of mobility and range of motion. During some of these activities the participant becomes wet or is submerged in water for all or most of the time. Some of these activities are done in cool weather. As a result, the participant is forced to wear heavier clothing or multiple layers, hence restricting his mobility and motion. This may shorten his time spent participating in the activity. For example, when diving in colder environments, the diver may wear a thicker wet suit. Another option is to purchase a dry suit, but they are expensive and require additional training to operate safely. Electric heaters are available for dry suits, but most are expensive and not easily recharged.

There are many heat packs utilizing a supercooled, supersaturated solution and a metallic activator to educe an exothermic phase change and warm the user. The solution and activator are stored inside a container, usually a plastic pouch, such that the solution is in contact with the activator. When the metallic activator is flexed, it initiates the crystallization process and heat is released. Once the crystallization process is complete, the container is heated, for example by boiling, melting the solution once more. After the solution is melted, the activator can be flexed again, starting the process over. For more information on how the metallic activator initiates the crystallization process, see Mansel A. Rogerson & Silvana S. Cardoso, *Solidification in Heat Packs: III. Metallic Trigger*, Vol. 49, No. 2 AIChE Journal 522 (Feb. 2003).

These heat packs are reliable, inexpensive, environmentally safe and easily recharged; however, the commercially available heat packs are not suitable to be activated under layers of clothing. For one thing, the heat packs are hard to access through multiple layers and, therefore, difficult to activate. Many of these heat packs require two hands to activate. Additionally, often the activator floats in the solution making it difficult to locate. As a result, the user must activate the heat pack before inserting it under layers of clothing in order to use it during diving or other such activity. It is desirable to activate the heat pack after spending some time participating in the activity, for example, when a diver descends into a colder depth of water.

SUMMARY OF INVENTION

The present invention discloses a reusable personal heating system attached to a garment to be worn under clothing which allows the wearer to participate in outdoor activities in cold conditions while permitting ease of mobility and range of motion. The invention comprises a reusable personal heating system including a sealed container, such as a plastic pouch, filled with a supercooled, supersaturated solution which releases heat during crystallization. The personal heating system also includes a crystallization activator which is located in a substantially fixed position within the container. A button that can be found and depressed through thick clothing is located in a fixed position above the activator. When the button is depressed, the activator flexes initiating the exothermic crystallization process. After the phase change is complete, the personal heating system can be heated, for instance by boiling, which will melt the solution. At this point the personal heating system can be reused.

The present invention further discloses a garment with multiple compartments that is worn under other clothes such as a wetsuit. The compartments are large enough to hold a personal heating system and large enough that the wearer can remove and replace a personal heating system while wearing the garment. The personal heating system fits into the compartment. The button on the personal heating system should face away from the wearer's body to make it easy to find the personal heating system.

The wearer can wear the garment under a thick wet suit or other clothing, insert personal heating systems in the compartments before starting an activity and activate the personal heating system through his outer clothing while participating in the activity without removing the personal heating system from the garment.

The present invention discloses a personal heating system that is safe, inexpensive, non-toxic, reusable and easily activated during an outdoor activity through multiple layers of outer wear. One advantage of the present invention is that it provides a push-button convenience for activation of a personal heating system containing a supercooled, supersaturated solution. Another advantage is that it allows the wearer to activate a heat pack through his clothing. Another advantage is that the activator and button are located in a fixed position in the heat pack.

DETAILED DESCRIPTION OF THE INVENTION

Figure 1:
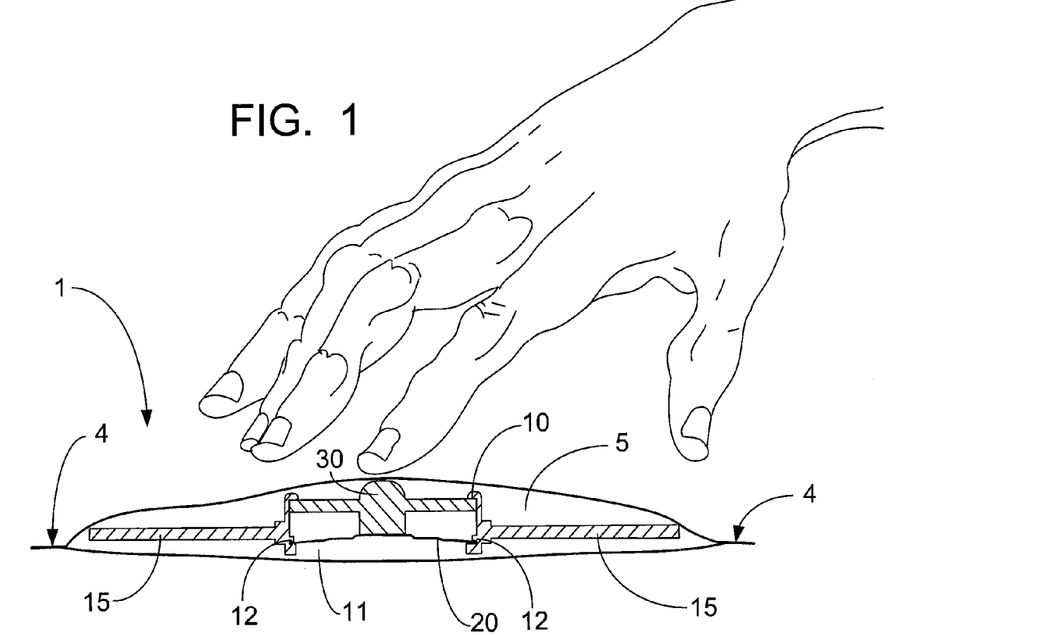
FIG. 1 shows a side view of one embodiment of the personal heating system.
Figure 2:
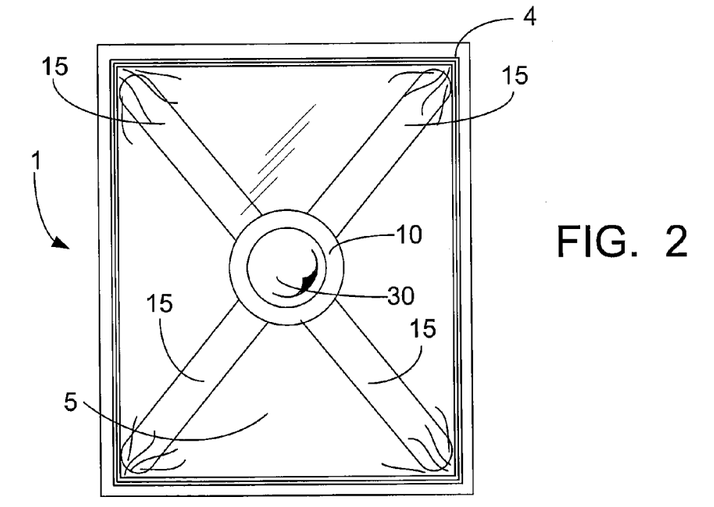
FIG. 2 shows a top view of on embodiment of the personal heating system and a means of suspending the holder in the solution.

Referring now to FIGS. 1 and 2, the present invention comprises a sealed container 1 holding a supercooled, supersaturated solution 5 which undergoes an exothermic phase change from liquid to solid. In one embodiment, the solution 5 is sodium acetate trihydrate, but it may be any other commercially available non-toxic, supercooled, supersaturated solution suitable for utilization in heat packs. The sealed container 1 is made of a flexible material, such as a plastic like polyvinylchloride (PVC). The container material must be suitable to withstand the heat required to melt the solution and the heat generated by the crystallization, but flexible enough that it does not restrict movement when worn as part of an active person's clothing A solution 5 is inside the container 1. The container 1 has a perimeter edge 4.

Figure 7:
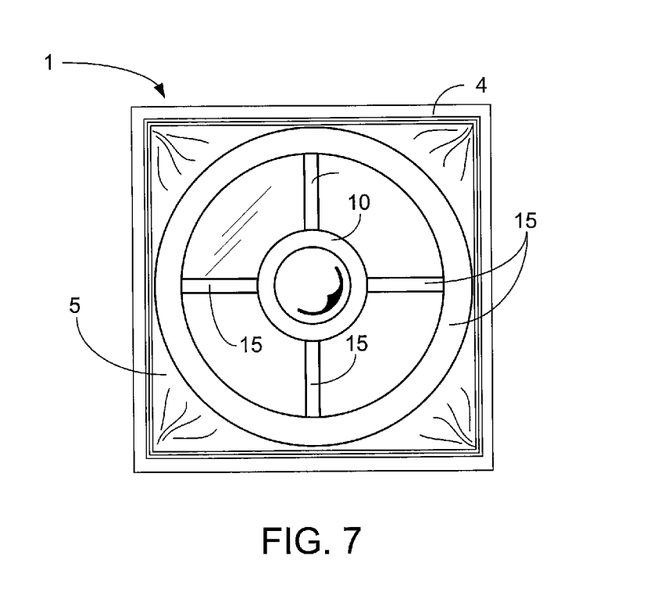
FIG. 7 shows a top view of one embodiment of the personal heating system including a means of suspending the holder in the solution.
Figure 18:
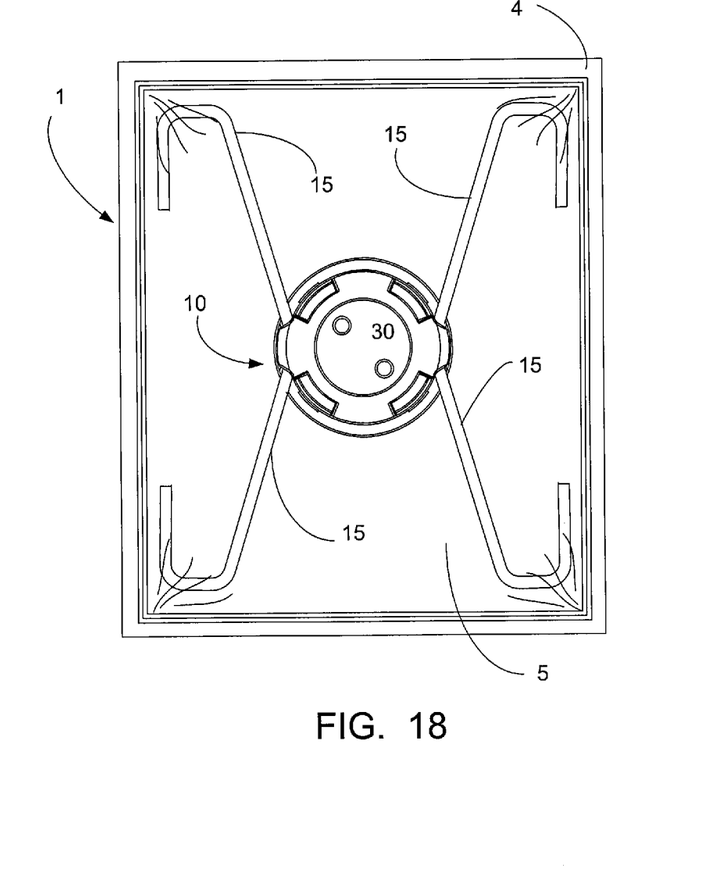
FIG. 18 shows a top view of one embodiment of the personal heating system including a means of suspending the holder in the solution.
Figure 19:
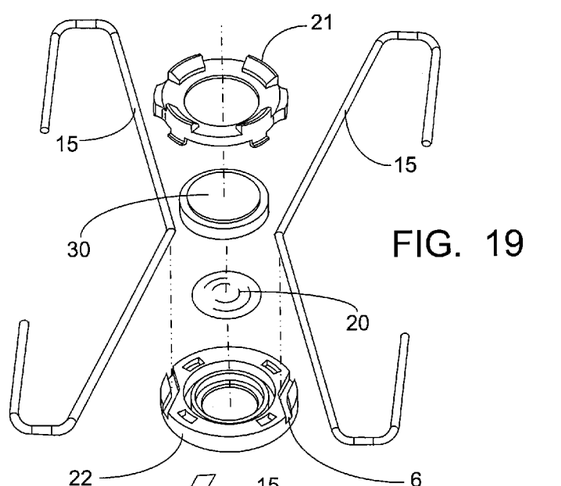
FIG. 19 shows an exploded view of one embodiment of the ribs, holder, button, and activator.
Figures 20, 21:
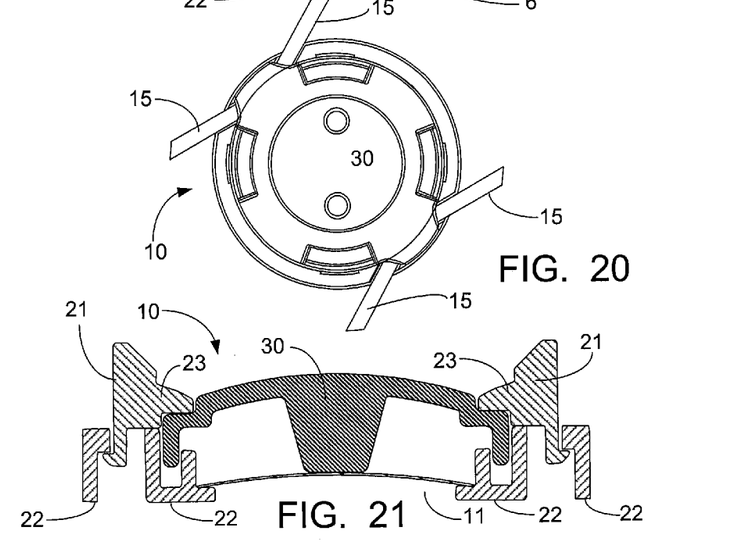
FIG. 20 shows a top view of one embodiment of the holder.
FIG. 21 shows a side view of one embodiment of the holder, activator and button.

An activator holder 10 with at least one opening 11 (FIG. 3) is located in a fixed position in said container 1 such that it is in contact with the solution 5. One embodiment includes a means for suspending said holder 10 in a fixed position in said solution 5. FIGS. 2 and 18 show one means for suspending holder 10 in a fixed position in said solution 5. A plurality of ribs 15 are attached to holder 10 and extend in various directions to the perimeter edge 4 of container 1. The ribs 15 float in solution 5. Any movement of the holder-rib assembly is minimal because the ribs 15 will hit the perimeter edge 4 of the container 1, thus holder 10 remains in position. The ribs 15 are made of a durable material which is compatible with solution 5, such as plastic. Those of skill in the art will recognize that there are many ways to attach the ribs 15 to the holder 10. Referring now to FIGS. 18, 19, and 20, in one embodiment, the ribs 15 fit into a ridge 6 in said holder 10 and extend in various directions from the holder 10 to the perimeter edge 4 of container 1. FIG. 7 shows another alternative means.

Figure 5:
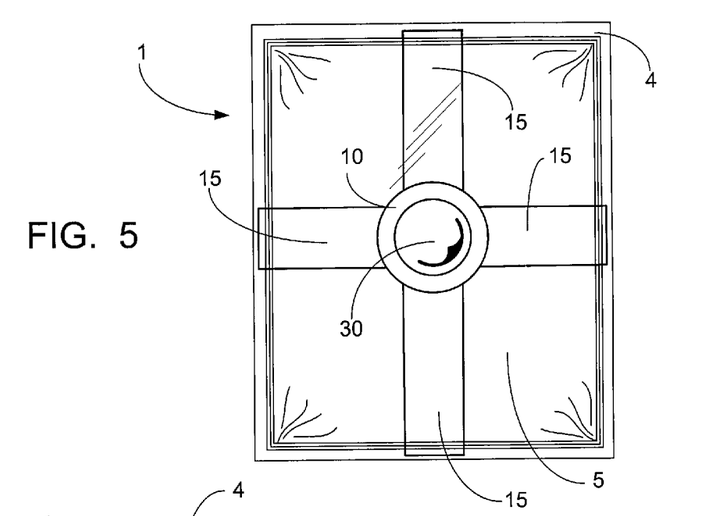
FIG. 5 shows a top view of one embodiment of the personal heating system including a means of suspending the holder in the solution.
Figure 6:
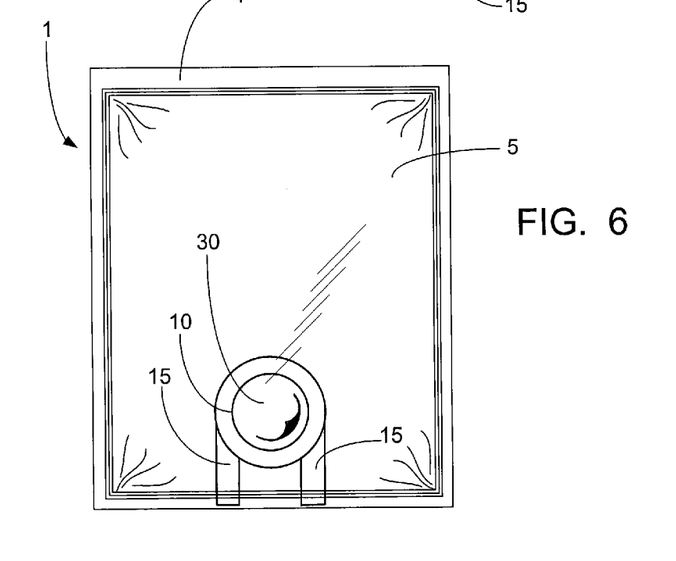
FIG. 6 shows a top view of one embodiment of the personal heating system including a means of suspending the holder in the solution.

FIGS. 5 and 6 show another means for suspending holder 10 in a fixed position in said solution 5. At least one rib 15 is attached to holder 10 and extends in various directions through the perimeter edge 4 of container 1. The perimeter edge 4 and the ribs 15 are adhered together by heat sealing or some similar process. These ribs 15 can be of any durable material capable of being heat sealed.

Figure 8:
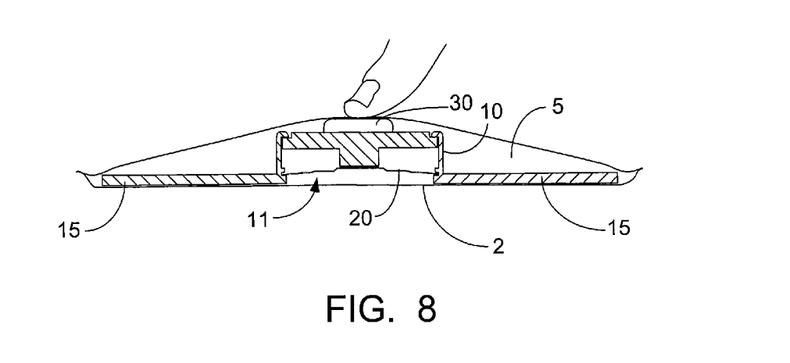
FIG. 8 shows a side view of one embodiment of the personal heating system where the ribs are attached to the a side of the container.

FIG. 8 shows another means for suspending holder 10 in a fixed position in said solution 5 where said ribs 15 are affixed to a side 2 of said container 1. Said holder 10 is attached to said ribs 15 such that said solution 5 is in contact with said opening 11. Those skilled in the art will recognize that there are many equivalent methods of suspending holder 10 in a fixed position in solution 5.

Figures 9, 10:
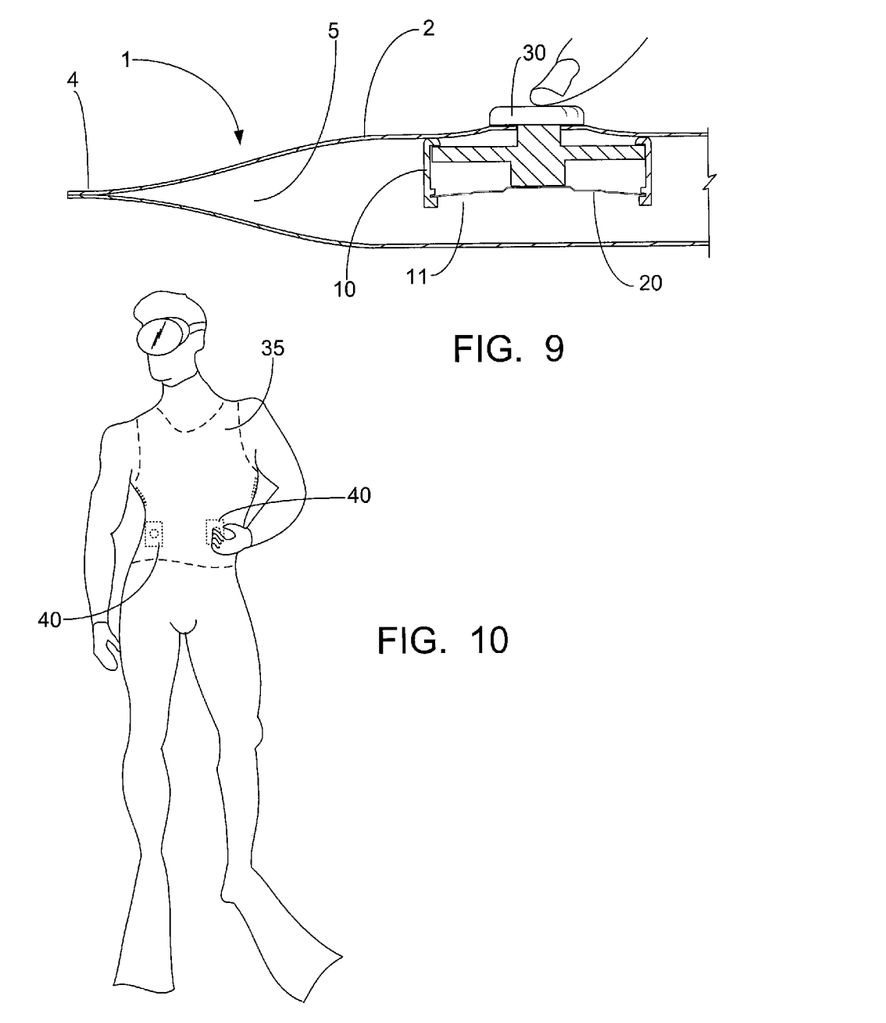
FIG. 9 shows a side view of one embodiment of the personal heating system where the holder is attached to the side of the container.
FIG. 10 shows a diver wearing one embodiment of the garment and activating the personal heating system through his wetsuit.

As shown in FIG. 9, in another embodiment, said holder 10 is immobile because it is attached to said side 2 of said container 1. The opening 11 of said holder 10 is in contact with said solution 5. Those skilled in the art will recognize that there are various methods of attaching said holder 10 to said side 2 such as gluing and welding.

Figure 3:
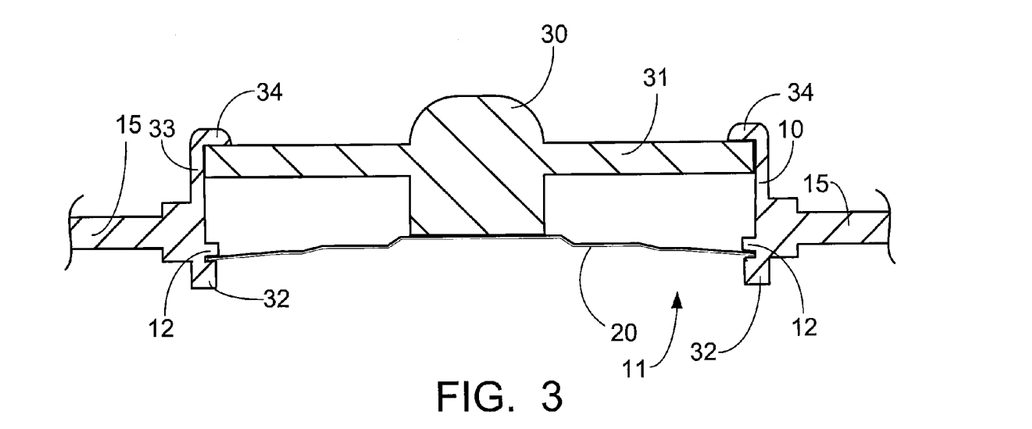
FIG. 3 shows a side view of one embodiment of the holder, activator and button.
Figure 15:
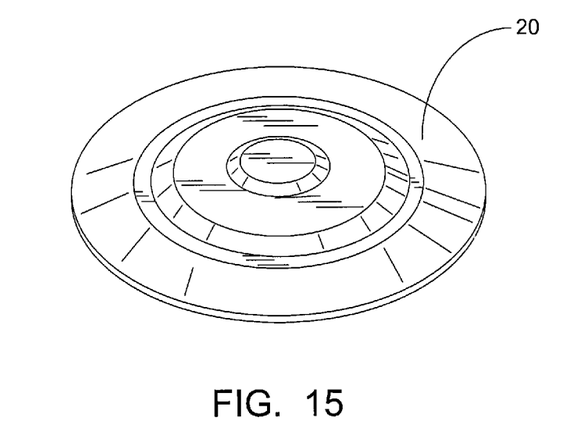
FIG. 15 shows one type of commercially available activator.

Referring now to FIG. 3, a commercially available crystallization activator 20 is mounted to holder 10 so that one side of activator 20 is adjacent to the opening 11. The activator 20 is in contact with the solution 5 through the opening 11. The activator 20 is selected from any of the commercially available activators used in heat packs. In one embodiment, the activator 20 is a flexible, stainless steel disk with a concave side and slits or indentations in its surface. An example of such an activator 20 is shown in FIG. 15. There are many methods of mounting the activator 20 in the holder 10 which are known to those skilled in the art. As shown in FIG. 3, in one embodiment the holder has a grooved edge 12 adjacent to said opening 11. The grooved edge 12 has dimensions such that the edges of the activator 20 fit securely under the grooved edge 12. The grooved edge 12 may protrude from the bottom of the holder 10 or it may be recessed into the bottom of holder 10. In another embodiment, the activator 20 is molded directly into the holder 10 adjacent into the opening 11. A first side of the activator 20 is in contact with solution 5 through opening 11. In yet another embodiment, as shown in FIGS. 19 and 21, the holder 10 has a top piece 21 and a bottom piece 22 with an opening 11. The top piece 21 is attached to the bottom piece 22. The activator 20 is disposed between said top piece 21 and said bottom piece 22 such that the activator 20 is in contact with the solution 5 through the opening 11.

Figure 4:
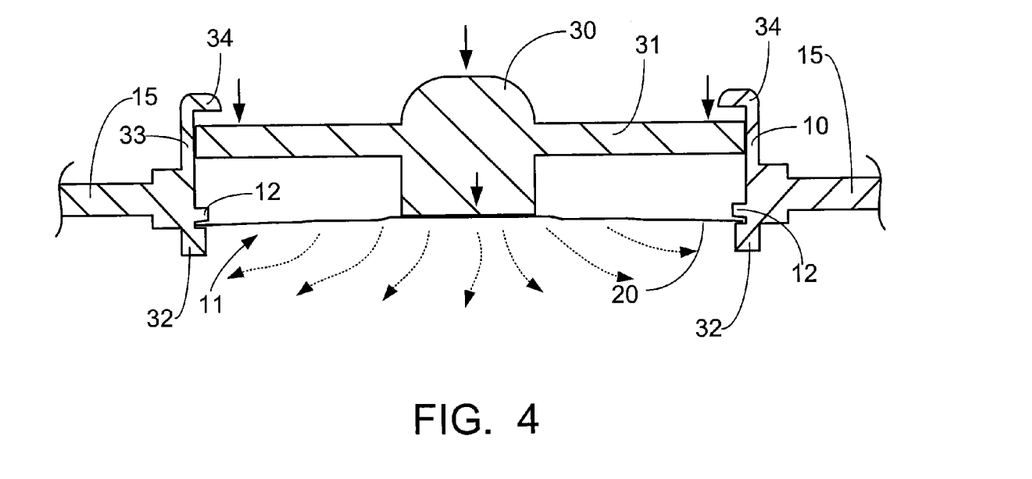
FIG. 4 shows a side view of the one embodiment of the holder, activator and button where the button is depressed and the activator is flexing.
Figure 11:
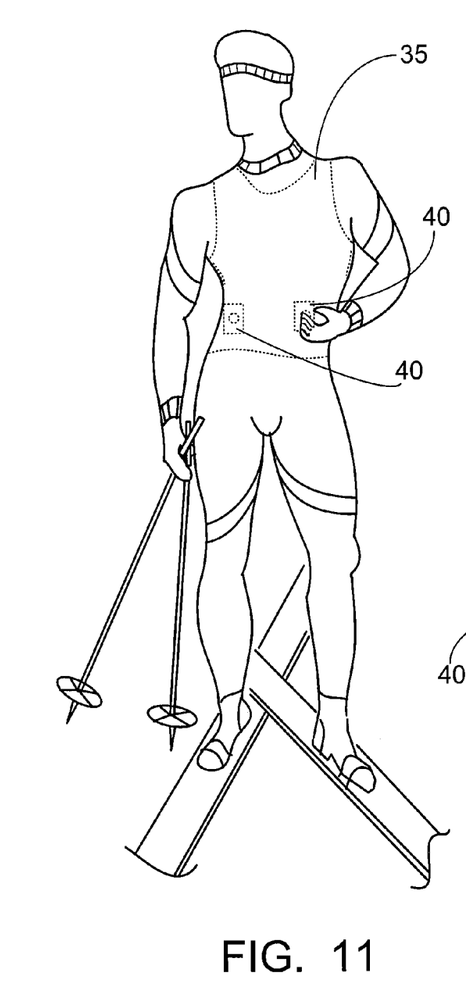
FIG. 11 shows a skier wearing one embodiment of the garment and activating the personal heating system through his wetsuit.

A button 30 is adjoined to said holder 10 and adjacent to second side of said activator 20. When the wearer presses on the button 30, the activator 20 flexes starting the crystallization process. (See FIG. 4) The button 30 is of sufficient hardness that it can be found and pressed through several layers of thick clothing. This allows the wearer to activate the personal heating system with one hand while participating in an outdoor activity as shown in FIGS. 10 and 11. Since assembly of the holder 10, the button 30, and activator 20 is in a substantially fixed location, it is possible for the wearer to activate the personal heating system with one hand while participating in an activity without having to locate the activator in the container.

There are many methods of placing the button 30 into the holder 10 which are known to those skilled in the art, for example molding, gluing or welding the button 30 onto the holder 10. As shown in FIG. 3, in one embodiment, the button 30 is attached to a top 31. Said holder 10 has a bottom 32 and a perimeter side 33 of a certain height attached to the perimeter edge of bottom 32. The top edge of perimeter side 33 had a ridge 34. The edge of said top 31 fits securely under said ridge 34. Said bottom 32 has an opening 11 and a grooved edge 12. Said activator 20 fits securely under said grooved edge 12. Alternatively as shown in FIG. 21, said holder 10 has a top piece 21 and a bottom piece 22. Said top piece 21 is attached to said bottom piece 22 and said activator 20 is disposed there between. The button 30 fits under a ridge 23 affixed to said top piece 21. The button 30 and activator 20 are positioned so that when said button 30 is depressed, it contacts said activator 20 which flexes and initiates the crystallization process.

Referring now to FIG. 9, in another embodiment, the button 30 is attached to a side 2 of said container 1 instead of being attached to said holder 10. Said holder 10 and activator 20 are in a fixed location adjacent to said button 30 such that said activator 20 is in contact with said solution 5. The holder 10 and activator 20 are positioned so that when said button 30 is depressed, it contacts said activator 20 which flexes and initiates the crystallization process.

Figure 12:
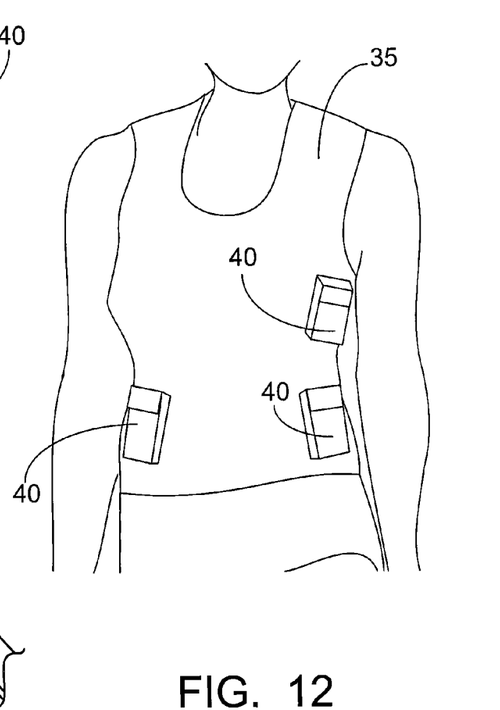
FIG. 12 shows one embodiment of the personal heating system attached to a garment.
Figure 13:
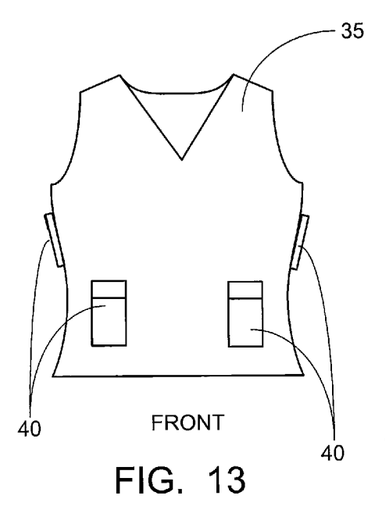
FIG. 13 shows a front view of one embodiment of the garment.
Figure 14:
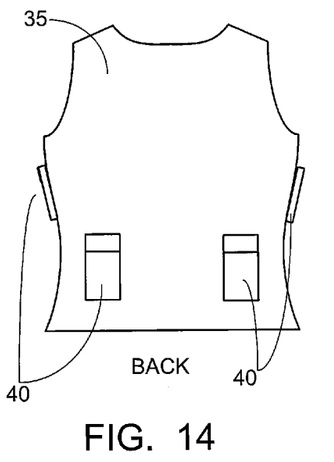
FIG. 14 shows a back view of one embodiment of the garment.

Referring now to FIGS. 12, 13 and 14, the present invention includes a garment 35 such as a shirt, vest, belt, harness or other similar apparel which is capable of being worn under other clothing such as a wet suit, sweater, snow suit or other similar clothing. (See FIGS. 10 and 11) The garment 35 can be made of any thin, durable material. In some embodiments, the garment 35 is made of lycra, neoprene, or the equivalent. Those skilled in the art will realize that other materials will also be suitable.

Figure 16:
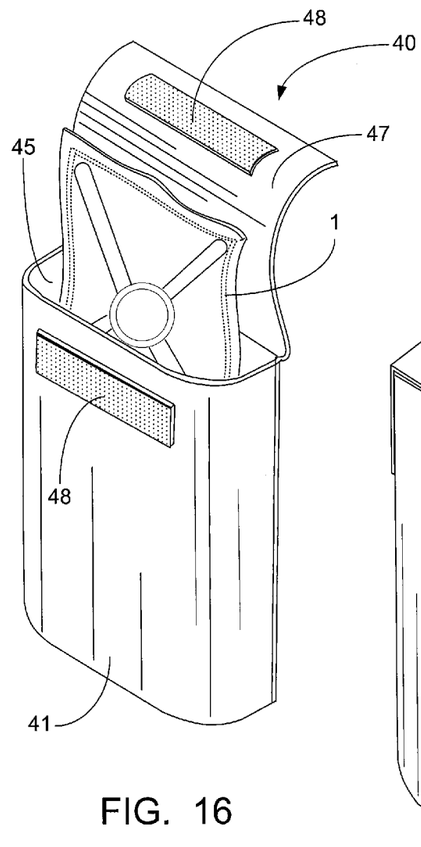
FIG. 16 shows a front view of the compartment that is attached to the garment to hold the personal heating system.
Figure 17:
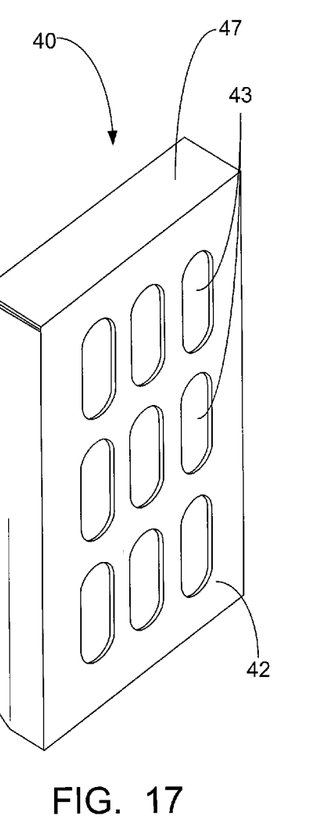
FIG. 17 shows a back view of one embodiment of the compartment that is attached to the garment to hold the personal heating system.

The garment 35 has at least one compartment 40 large enough to enclose the container 1. Referring now to FIGS. 16 and 17, the compartment 40 has at least one side 41 attached to garment 35. The compartment 40 has at least one opening 45 where the container 1 can be inserted or removed from the compartment 40. If the container 1 is inserted into the compartment 40 so that the button 30 is adjacent to the side 41, it is easier for the wearer to depress the button 30 through his clothing. The compartments 40 are of sufficient size that the container 1 can be easily removed or replaced into the compartment 40 while the wearer is wearing the garment 35.

There is a closure mechanism 46 attached to the opening 45 so that the opening 45 may be closed thus securing the container 1 inside the compartment 40 while the wearer is active. The closure mechanism 46 may be any number of common closure devices such as Velcro, snaps, zippers, or the like. In one embodiment, the closure mechanism 46 is corrosion resistant.

In one embodiment, the closure mechanism 46 may consist of a flap 47 and a fastener 48. The first end of said flap 47 is attached to said compartment 40 adjacent to said opening 45. The second end of said flap 47 extends over said opening 45, covering said opening 45. The fastener 48 is affixed to the opposite side of the compartment 40 as the first end of said flap 47. The second end of said flap 47 is secured to the compartment 40 by said fastener 48. The fastener 48 may be any number of common closure devices such as Velcro, snaps, zippers, or the like. In one embodiment, the fastener 48 is corrosion resistant.

The compartments are also made of a durable material, but are of sufficient thickness to keep the containers well insulated from the surrounding environment. In some embodiments, the compartments 40 are made of lycra, neoprene, or some similar material. In one embodiment, portion of the garment 35 where the side 41 of the compartment 40 is attached is thinner than the rest of the compartment 40 to allow for efficient heat transfer through the garment 35 to the wearer. In one embodiment, the portion of the garment 35 where the side 41 of the compartment 40 is attached includes at least one aperture 43 to allow for increased heat transfer through the garment 35 to the wearer. (See FIG. 17)

In another embodiment, a side 41 of the compartment 40 includes at least one aperture 43. In still another embodiment, the compartment 40 is attached to the interior of the garment 35 such that the container 1 is intermediate to the garment 35 and the wearer's body. In yet another embodiment, the compartment 40 is attached to the exterior of the garment 35 such that the garment 35 is intermediate to the container 1 and the wearer's body.

Referring now to FIGS. 10, 11 and 12, in one embodiment, there are at least four (4) compartments 40 on said garment 35. The compartments 40 may be located anywhere on the garment 35. Suggested locations are under the armpits or on the back over the kidneys.

The present invention is reusable because after crystallization is complete and no more heat is being generated, the container 1 may be heated, for example by boiling, to melt the crystals. This regenerates the container 1 and it can be used again. The garment 35 is also reusable because once crystallization is complete, the container 1 can be removed from the compartment 40 and replaced with a new or regenerated container 1.

What is claimed is:

1. A personal heating system comprising:
    a sealed container having a perimeter edge, said container surrounding a supercooled, supersaturated solution which releases heat upon crystallization;
    an activator holder having at least one opening, said holder enclosed in said container and suspended in said solution;
    at least one rib having a first end and a second end, said first end attached to said holder, said second end extending to adjacent said perimeter edge such that said holder is disposed in a substantially fixed relationship with said perimeter edge of said container;
    a crystallization activator having at least one surface, said activator connected to said holder and positioned such that said at least one surface of said activator is in contact with said solution via said opening in said holder; and
    a button moveably engaged with said holder and adjacent to said activator, said button capable of contacting said activator when depressed thereby causing said activator to flex.

2. The personal heating system of claim 1 where:
    said container has a first corner, a second corner, a third corner and a fourth corner;
    a first rib having a first end and a second end, said first end attached to said holder, said second end extending to adjacent said first corner such that said holder is disposed in a substantially fixed relationship with said first corner of said container;
    a second rib having a first end and a second end, said first end attached to said holder, said second end extending to adjacent said second corner such that said holder is disposed in a substantially fixed relationship with said second corner of said container;
    a third rib having a first end and a second end, said first end attached to said holder, said second end extending to adjacent said third corner such that said holder is disposed in a substantially fixed relationship with said third corner of said container; and
    a fourth rib having a first end and a second end, said first end attached to said holder, said second end extending to adjacent said fourth corner such that said holder is disposed in a substantially fixed relationship with said forth corner of said container.

3. The personal heating system of claim 1 further comprising:
- a garment having at least one compartment for receiving said container;
- said compartment having at least one opening; and
- at least one closure mechanism attached to said compartment and adjacent to said opening for securing said container inside said compartment.

4. The personal heating system of claim 3 further comprising:
- at least one aperture in said garment adjacent to said compartment and said container allowing increased heat transfer through said garment.

5. The personal heating system of claim 3 where said closure mechanism further comprises:
- a flap with a first end and a second end, said first end attached to said compartment adjacent to said opening, said flap for covering said opening; and
- a fastener affixed to said compartment for securing said second end of said flap to said compartment.

6. The personal heating system of claim 1 where:
- said holder has a top piece and a bottom piece, said top piece attached to said bottom piece, said bottom piece having at least one opening;
- said activator intermediate to said top piece and said bottom piece such that said surface of said activator is in contact with said solution through said opening;
- said button movably engaged with said top piece of said holder, said button capable of contacting said activator when depressed thereby causing said activator to flex.

7. The personal heating system of claim 1 where:
- said second end of said at least one rib is attached to said container at said perimeter edge such that said holder is disposed in a substantially fixed relationship with said perimeter edge of said container.

8. The personal heating system of claim 1 where:
- said at least one rib is attached to a side of said container.

9. A personal heating system comprising:
- a sealed container having a plurality of sides, said container surrounding a supercooled, supersaturated solution which releases heat upon crystallization;
- an activator holder having at least one opening, said holder affixed to a first side of said container;
- a crystallization activator having at least one surface, said activator connected to said holder and positioned such that said at least one surface of said activator is in contact with said solution via said opening in said holder; and
- a button moveably engaged with said holder and adjacent to said activator, said button capable of contacting said activator when depressed thereby causing said activator to flex.

10. The personal heating system of claim 9 further comprising:
- a garment having at least one compartment for receiving said container;
- said compartment having at least one opening; and
- at least one closure mechanism attached to said compartment and adjacent to said opening for securing said container inside said compartment.

11. The personal heating system of claim 10 further comprising:
- at least one aperture in said garment adjacent to said compartment and said container allowing increased heat transfer through said garment.

12. The personal heating system of claim 10 where said closure mechanism further comprises:
- a flap with a first end and a second end, said first end attached to said compartment adjacent to said opening, said flap for covering said opening; and
- a fastener affixed to said compartment for securing said second end of said flap to said compartment.

13. The personal heating system of claim 9 where:
- said holder has a top piece and a bottom piece, said top piece attached to said bottom piece, said bottom piece having at least one opening;
- said activator intermediate to said top piece and said bottom piece such that said surface of said activator is in contact with said solution through said opening;
- said button movably engaged with said top piece of said holder, said button capable of contacting said activator when depressed thereby causing said activator to flex.

14. The personal heating system of claim 9 where:
- said container has an exterior and an interior; and
- said button is affixed to said exterior of said container and aligned with said holder and said activator, said button capable of causing said activator to flex when depressed.

* * * * *